United States Patent [19]

DeBernardis et al.

[11] Patent Number: 4,963,563
[45] Date of Patent: Oct. 16, 1990

[54] 6-SUBSTITUTED-1,2,3,4-TETRAHYDROISOQUINOLINES

[75] Inventors: John F. DeBernardis, Lindenhurst; Robert E. Zelle, Grayslake, both of Ill.

[73] Assignee: Abbott Laboratories, Abbott Park, Ill.

[21] Appl. No.: 421,213

[22] Filed: Oct. 13, 1989

[51] Int. Cl.$^5$ .................... A61K 31/47; C07D 409/06
[52] U.S. Cl. .................... 514/307; 514/310; 546/143; 546/146; 546/147; 546/148; 546/149
[58] Field of Search ............... 546/143, 146, 147, 148, 546/149; 514/307, 310

[56] References Cited

U.S. PATENT DOCUMENTS 4,261,998 4/1981 Najer ................................. 546/146
4,766,131 8/1988 Davidson et al. ................ 546/149
4,885,302 12/1989 George et al. .................... 546/146

Primary Examiner—Richard L. Raymond
Assistant Examiner—James H. Turnipseed
Attorney, Agent, or Firm—Steven F. Weinstock

[57] ABSTRACT

Compounds of the formula:

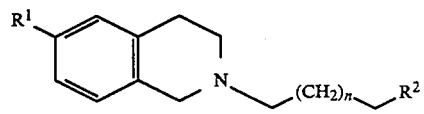

wherein $n = 1$ or 2; $R_1$ is lower alkoxy, lower alkyl, halo, ester, carbamate, or substituted amino; and $R_2$ is thienyl or furyl; or $R_2$ is

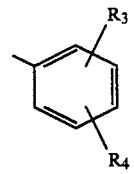

wherein $R_3$ and $R_4$ are independently selected from hydrogen, halo, hydroxy, methoxy, thioalkoxy, substituted amino and lower alkyl; and pharmaceutically acceptable salts thereof.

These compounds are useful as inhibitors of alpha-2-adrenergic receptors and for the treatment of glaucoma and/or controlling intraocular pressure.

7 Claims, No Drawings

6-SUBSTITUTED-1,2,3,4-TETRAHYDROISOQUINOLINES

TECHNICAL FIELD

This invention relates to alpha-2-adrenergic antagonists useful in the treatment of depression, metabolic disorders such as obesity or diabetes, glaucoma, migraine and hypertension.

BACKGROUND OF THE INVENTION

The adrenergic nervous system plays a major role in the innervation of heart, blood vessel and smooth muscle tissue. Compounds capable of interacting with receptor sites within the adrenergic nervous system can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within the adrenergic nervous system in order to obtain a desired physiological response separate from the other possible, and perhaps less undesirable, responses of the system.

SUMMARY OF THE INVENTION

It has been determined that a new class of compounds, as herein defined, demonstrate an ability to selectively inhibit (antagonists) alpha-2-adrenergic receptors which are mainly distributed on the membranes of central and peripheral adrenergic neurons and on the tissues innervated thereby.

Through inhibitory interaction with the alphaadrenergic receptor in the peripheral nervous system, one can modulate the function of adrenergic neurons and hemodynamic equilibrium which is therapeutically useful in a multitude of cardiovascular indications such as hypertension, congestive heart failure, and a variety of muscular spastic conditions. Furthermore, the alphaadrenergic antagonists are useful in certain neurological and psychiatric disorders such as depression.

The present invention is directed to compounds represented by Formula I:

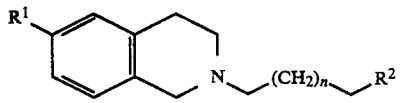

wherein n=1 or 2; $R_1$ is lower alkoxy, lower alkyl, halo, ester, carbamate, or substituted amino; and $R_2$ is thienyl or furyl; or $R_2$ is

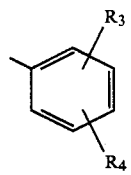

wherein $R_3$ and $R_4$ are independently selected from hydrogen, halo, hydroxy, methoxy, thioalkoxy, substituted amino and lower alkyl; and pharmaceutically acceptable salts thereof.

This invention also relates to pharmaceutical compositions and methods of selectively inhibiting alpha-2-adrenergic receptors and diseases such as metabolic disorders, depression, glaucoma, migraine and hypertension, comprising the administration to a mammal, preferably a human in need of such treatment of a compound of Formula I.

DETAILED DESCRIPTION OF THE INVENTION

The present invention is directed to compounds represented by Formula I:

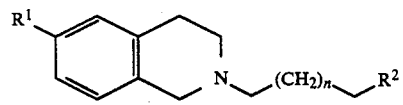

wherein n=1 or 2; $R_1$ is lower alkoxy, lower alkyl, halo, ester, carbamate, or substituted amino; and $R_2$ is thienyl or furyl; or $R_2$ is

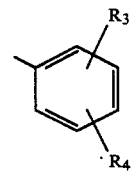

wherein $R_3$ and $R_4$ are independently selected from hydrogen, halo, hydroxy, methoxy, thioalkoxy, substituted amino and lower alkyl; and pharmaceutically acceptable salts thereof.

Presently preferred compounds of Formula I include:
1,2,3,4-tetrahydro-6-methoxy-N-3-(2-thienyl) propylisoquinoline hydrochloride;
1,2,3,4-tetrahydro-6-methoxy-N-4-(2-thienyl) butylisoquinoline hydrochloride; and
1,2,3,4-tetrahydro-6-methyl-N-3-(2-thienyl) propylisoquinoline hydrochloride.

This invention also relates to pharmaceutical compositions and methods of selectively inhibiting alpha-2-adrenergic receptors and diseases such as metabolic disorders, depression, migraine, hypertension, glaucoma and reducing and/or controlling intraocular pressure comprising the administration to a mammal, preferably a human in need of such treatment of a compound of Formula I.

As used herein, the term "lower alkoxy" refers to straight and branched chain oxygen ether radicals having 1 to 4 carbon atoms, such as methoxy, ethoxy, isopropoxy, n-butoxy, sec-butoxy, isobutoxy and t-butoxy.

As used herein, the term "lower alkyl" refers to straight or branched chain saturated hydrocarbons having 1 to 3 carbon atoms, such as methyl, ethyl, n-propyl and isopropyl.

As used herein, the term "thioalkoxy" refers to —$SR_5$ wherein $R_5$ is lower alkyl.

As used herein, the term "halo" or "halogen" refers to fluorine, chlorine, bromine or iodine.

As used herein, the term "substituted amino" refers to $NR_6R_7$ wherein $R_6$ and $R_7$ are independently selected from hydrogen, lower alkyl or —$SO_2CH_3$.

As used herein, the term "ester" refers to OC(O)$R_8$ wherein $R_8$ is lower alkyl, phenyl, cyclohexyl or tert-butyl.

As used herein, the term "carbamate" refers to OC(O)$NR_6R_7$ wherein $R_6$ and $R_7$ are independently selected from hydrogen or lower alkyl.

As used herein, the term "pharmaceutical acceptable salts" refers to the pharmaceutically acceptable, relatively nontoxic, inorganic or organic acid addition salts of the compounds of this invention. These salts can be prepared in situ during the final isolation and purification of the compounds, or by separately reacting the free base with a suitable organic or inorganic acid. Representative salts include the hydrochloride, hydrobromide, sulfate, phosphate, nitrate, bisulfate, acetate, oxalate, valerate, oleate, palmitrate, methanesulfonate, stearate, laurate, borate, benzoate, lactate, tosylate, citrate, maleate, fumarate, succinate, tartrate, napsylate, and the like. It will be apparent to those skilled in the art that, depending upon the number of available amino groups for salt formation, the salts of this invention can be per-N-salts.

Certain compounds of this invention may exist in optically active forms. The R and S isomers and mixtures thereof, including racemic mixtures as well as the cis and trans mixtures are contemplated by this invention. Additional asymmetric carbon atoms may be present in a substituent group such as an alkyl group. All such isomers as well as the mixtures thereof are intended to be included in the invention.

The present invention includes one or more of the compounds of Formula I formulated into compositions together with one or more non-toxic pharmaceutically acceptable carriers, adjuvants or vehicles which are collectively referred to herein as carriers, for parenteral injection, for oral administration in solid or liquid form, for rectal administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethylene glycols, and the like.

Solid dosage forms such as tablets, dragees, capsules, pills and granules can be prepared with coatings and shells, such as enteric coatings and others well known in this art. They may contain opacifying agents, and can also be of such composition that they release the active compound or compounds in a certain part of the intestinal tract in a delayed manner. Examples of embedding compositions which can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of this invention with suitable nonirritating excipients or carriers such as cocoa butter, polyethylene glycol or a suppository wax, which are solid at ordinary temperatures but liquid at body temperature and, therefore, melt in the rectum or vaginal cavity and release the active component.

Dosage forms for topical administration of a compound of this invention include powders, sprays and inhalants. The active component is admixed under sterile conditions with a pharmaceutically acceptable carrier and any needed preservatives, buffers or propellants as may be required. Ophthalmic formulations, eye ointments, powders and solutions are also contemplated as being within the scope of this invention.

Compositions for treating glaucoma and reducing and/or controlling intraocular pressure are administered as topical or systemic pharmaceutical compositions. These compositions are preferably administered as topical pharmaceutical compositions suitable for ophthalmic administration, in a pharmaceutical vehicle such as pharmaceutically acceptable sterile aqueous or nonaqueous solutions, suspensions, emulsions, ointments and solid inserts.

Examples of suitable pharmaceutically acceptable vehicles for ophthalmic administration are water, propylene glycol and other pharmaceutically acceptable alcohols, sesame or peanut oil and other pharmaceutically acceptable oils, petroleum jelly, water soluble ophthalmically acceptable non-toxic polymers such as methyl cellulose, carboxymethyl cellulose salts, hydroxyethyl cellulose, hydroxypropyl cellulose; acrylates such as polyacrylic acid salts; ethylacrylates; polyacrylamides; natural products such as gelatin, alginates, pectins, tragacanth, karaya, agar acacia; starch derivatives such as starch acetate, hydroxyethyl starch ethers, hydroxypropyl starch; as well as other synthetic derivatives such as polyvinyl alcohol, polyvinyl pyrrolidone, polyvinyl methyl ether, polyethylene oxide, carbopol and xanthan gum; and mixture of these polymers. Such compositions may also contain adjuvants such as buffering, preserving, wetting, emulsifying and dispersing agents. Suitable preserving agents include antibacterial agents such as quaternary ammonium compounds, phenylmercuric salts, benzyl alcohol, phenyl ethanol; and antioxidants such as sodium metabisulfite, butylated hydroxyanisole and butylated hydroxytoluene. Suitable buffering agents include borate, acetate, gluconate and phosphate buffers.

The pharmaceutical ophthalmic compositions of the invention may also be in the form of a solid insert. A solid water soluble or water swellable polymer such as dextran, hydroxyloweralkyl dextran, carboxymethyl dextran, hydroxyloweralkyl cellulose, loweralkyl cellulose, carboxymethyl cellulose, polyvinyl alcohol, dextrin, starch, polyvinyl pyrrolidone and polyalkylene glycols may be used as the carrier for the drug.

Dosage levels of the active compound in the compositions for treating glaucoma or reducing and/or controlling intraocular pressure may be varied so as to obtain a desired therapeutic response to a particular composition. Generally, the active compound will be administered as an isotonic aqueous solution of from 0.01 to 1.0 (w/v) percent concentration. More preferably, the active compound will be administered as an isotonic aqueous solution of from 0.01 to 0.3 (w/v) percent concentration.

The term "controlling intraocular pressure" as used herein means the regulation, attenuation and modulation of increased intraocular tension. The term also means that the decrease, in the otherwise elevated intraocular pressure, obtained by the methods and compositions of the invention is maintained for a significant period of time as, for example, between consecutive doses of the ophthalmic compositions of the present invention.

The present compounds can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the alpha-2-adrenergic compounds of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

Actual dosage levels of active ingredient in the compositions of the invention may be varied so as to obtain an amount of active ingredient that is effective to obtain a desired therapeutic response for a particular composition and method of administration. The selected dosage level, therefore, depends upon the desired therapeutic effect, on the route of administration, on the desired duration of treatment and other factors.

Total daily dose of the compounds of this invention administered to a host in single or divided doses may be in amounts, for example, of from about 0.1 to about 200 mg/kg body weight daily, preferably about 0.5 to about 150 mg/kg/day and more preferably about 1 to about 125 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The compounds of the present invention can be prepared as illustrated in Scheme 1.

SCHEME 1

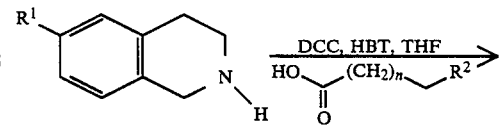

-continued
SCHEME 1

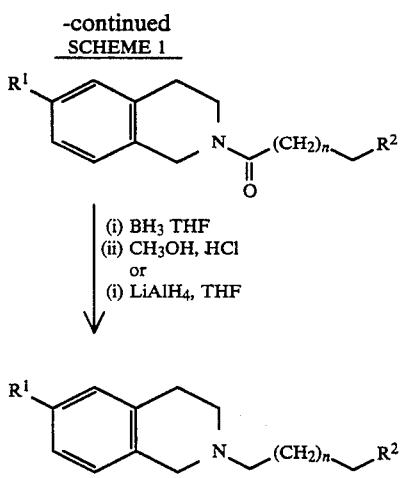

(i) BH₃ THF
(ii) CH₃OH, HCl
or
(i) LiAlH₄, THF

As seen in Scheme 1, dicyclohexylcarbodiimide (DCC) coupling of 1,2,3,4-tetrahydroisoquinoline derivatives with the appropriate carboxylic acid provides the corresponding amide. Reduction of the resulting amide with either diborane or lithium aluminum hydride (LiAlH₄) provides the desired N-substituted tetrahydroisoquinoline.

The foregoing may be better understood in connection with the following examples:

EXAMPLE 1

1,2,3,4-Tetrahydro-6-methoxy-N-3-(2-thienyl)propionylisoquinoline

To a solution of 1,2,3,4-tetrahydro-6-methoxyisoquinoline (3.29 g), hydroxybenzotriazole monohydrate (5.72 g) and 3-(2-thienyl)propanoic acid (3.31 g) in 280 ml of dry tetrahydrofuran (THF) at 0° C. was added DCC (4.37 g) in one portion. The reaction was allowed to warm to room temperature and stirred overnight. The reaction was filtered and concentrated. The residue was taken up into 200 ml of ethyl acetate (EtOAc) refiltered, washed with 5% aq. HCl (50 ml), 5% aq. NaCl (50 ml), 10% aq. KOH (50 ml), dried (MgSO₄), filtered, and concentrated. Chromatography on silica gel (elution with 20% EtOAc:hexanes) afforded 4.54 g of the desired product.

EXAMPLE 2

1,2,3,4-Tetrahydro-6-methoxy-N-3-(2-thienyl)propylisoquinoline hydrochloride

To a solution of the product of Example 1 in dry THF (100 ml) was added a 1.0 M solution of borane tetrahydrofuran complex (26.6 ml) and the resulting solution heated to reflux. After 1 hour, the reaction was cooled to room temperature and slowly quenched with a saturated methanolic HCl solution (40 ml). The reaction was then refluxed for 45 minutes, cooled to room temperature and concentrated. The residue was dissolved in a minimum amount of methanol and slowly diluted with Et₂O, upon which a white precipitate formed. The solid was collected, washed with Et₂O and dried under vacuum at 60° C. to afford 3.31. g of desired product. m.p. 208°–209° C. Anal. calcd. for $C_{17}H_{21}NOS \cdot HCl$: C, 63.04; H, 6.85; N, 4.32. Found: C, 63.19; H, 6.88; N, 4.31.

EXAMPLE 3

1,2,3,4-Tetrahydro-6-methoxy-N-4-(2-thienyl)butionylisoquinoline

Using the procedure of Example 1, but replacing 3-(2-thienyl)propanoic acid with 4-(2thienyl)butyric acid provided the desired product.

EXAMPLE 4

1,2,3,4-Tetrahydro-6-methoxy-N-4-(2-thienyl)-butylisoquinoline hydrochloride

To a suspension of lithium aluminum hydride (988 mg) in dry THF (40 ml) was slowly added a solution of the product of Example 3 (4.10 g) in THF (15 ml), and the reaction heated to reflux. After 2.5 hours at reflux, the reaction was cooled to room temperature and slowly quenched with water (1 ml), 15% aq. KOH (1 ml), followed by an additional 3.0 ml of water. After stirring for 1 hour, the reaction was dried (MgSO₄), filtered and concentrated to afford 3.44 g of product as a viscous oil. The oil was dissolved into EtOAc and treated with methanolic HCl upon which a white precipitate formed. The solid was collected, dried under vacuum at 60° C. to provide the desired product. m.p. 173°–174° C. Anal. calcd. for $C_{18}H_{23}NOS \cdot HCl$: C, 63.98; H, 7.16; N, 4.15. Found: C, 64.01; H, 7.09; N, 4.18.

EXAMPLE 5

1,2,3,4-Tetrahydro-6-methoxy-N-3-(m-fluorophenyl)propyl isoquinoline hydrochloride Using the procedures of Examples 1 and 4, but replacing 3-(2-thienyl)propanoic acid with 3-(m-fluorophenyl)propanoic acid provided the desired product. m.p. 210°–211° C. Anal. calcd. for $C_{19}H_{22}FNO \cdot HCl$: C, 67.95; H, 6.90; N, 4.17. Found: C, 67.81; H, 6.97; N, 4.12.

EXAMPLE 6

1,2,3,4-Tetrahydro-6-methoxy-N-3-(2-furyl)-propylisoquinoline hydrochloride

Using the procedures of Examples 1 and 4, but replacing 3-(2-thienyl)propanoic acid with 3-(2-furyl)-propanoic acid provided the desired product. m.p. 195°–196° C. Anal. calcd. for $C_{17}H_{21}NO_2 \cdot HCl$: C, 68.65; H, 8.07; N, 4.00. Found: C, 69.02; H, 8.05; N, 4.04.

EXAMPLE 7

1,2,3,4-Tetrahydro-6-methoxy-N-(3-phenylpropyl)isoquinoline hydrochloride

Using the procedures of Examples 1 and 2, but replacing 3-(2-thienyl)propanoic acid with 3-phenylpropanoic acid afforded the desired product. m.p. 211°–212° C. Anal. calcd. for $C_{19}H_{23}HO \cdot HCl$: C, 71.80; H, 7.61; N, 4.41. Found: C, 72.09; H, 7.63; N, 4.32.

EXAMPLE 8

1,2,3,4-Tetrahydro-6-methoxy-N-3-(3-methoxyphenyl)-propyl isoquinoline hydrochloride Using the procedures of Examples 1 and 2, but replacing 3-(2-thienyl)propanoic acid with 3-(3-methoxyphenyl)propanoic acid afforded the desired product. m.p. 184°–185° C. Anal. calcd. for $C_{20}H_{25}NO_2 \cdot HCl$: C, 69.05; H, 7.53; N, 4.03. Found: C, 68.88; H, 7.55; N, 4.07.

EXAMPLE 9

1,2,3,4-Tetrahydro-6-methoxy-N-3-(2-methoxyphenyl)-propyl isoquinoline hydrochloride Using the procedures of Examples 1 and 2, but replacing 3-(2-thienyl)propanoic acid with 3-(2-methoxyphenyl)propanoic acid afforded the desired product. m.p. 155°–156° C. Anal. calcd. for $C_{20}H_{25}NO_2 \cdot HCl$: C, 69.05; H, 7.53; N, 4.03. Found: C, 69.11; H, 7.69; N, 4.05.

EXAMPLE 10

1,2,3,4-Tetrahydro-6-methoxy-N-(4-phenylbutyl-)isoquinoline methane sulfonate Using the procedures of Examples 1 and 2, but replacing 3-(2-thienyl)propanoic acid with 4-phenylbutanoic acid afforded the hydrochloride salt. The hydrochloride salt was converted to the free base and dissolved into EtOAc, and treated with a solution of methanesulfonic acid in EtOAc. A solid separated, which was filtered to give rise to the desired product. m.p. 148°–149° C. Anal. calcd. for $C_{20}H_{25}NO \cdot CH_3SO_3H$: C, 64.42; H, 7.47; N, 3.58. Found: C, 64.33; H, 7.57; N, 3.55.

EXAMPLE 11

1,2,3,4-Tetrahydro-6-methoxy-N-3-(3-chlorophenyl)-propyl isoquinoline methanesulfonate Using the procedures of Examples 1 and 2, but replacing 3-(2-thienyl)propanoic acid with 3-(3-chlorophenyl)propanoic acid afforded the hydrochloride salt. The hydrochloride salt was converted to the methanesulfonate salt as described in Example 10 to afford the desired product. m.p. 122° C. Anal. calcd. for $C_{19}H_{22}ClNO \cdot CH_3SO_3H$: C, 58.31; H, 6.36; N, 3.40. Found: C, 58.49; H, 6.46; N, 3.38.

EXAMPLE 12

1,2,3,4-Tetrahydro-6-methyl-N-3-(2-thienyl)-propylisoquinoline Hydrochloride Using the procedures of Examples 1 and 2, but replacing 1,2,3,4-tetrahydro-6-methoxyisoquinoline with 1,2,3,4-tetrahydro-6-methylisoquinoline provided the desired product. m.p. 220°–221° C. Anal. calcd. for $C_{17}H_{21}NS \cdot HCl \cdot H_2O$: C, 62.65; H, 7.42; N, 4.30. Found: C, 3.08; H, 7.17; N, 4.30.

EXAMPLE 13

1,2,3,4-Tetrahydro-6-methyl-N-(3-(phenyl-propylisoquinoline Hydrochloride

Using the procedures of Examples 1 and 2, but replacing 1,2,3,4-tetrahydro-6-methoxyisoquinoline with 1,2,3,4-tetrahydro-6-methylisoquinoline and 3-(2-thienyl)propanoic acid with 3-phenylpropanoic acid provided the desired product. m.p. 235°–236° C. Anal. calcd. for $C_{19}H_{23}N \cdot HCl \cdot H_2O$: C, 71 34; H, 8.19; N, 4.38. Found: C, 71.25; H, 7.79; N, 4.37.

EXAMPLE 14

1,2,3,4,-Tetrahydro-6-hydroxy-N-3-(2-thienyl)propionylisoquinoline

A suspension of 1,2,3,4-tetrahydro-6-hydroxyisoquinoline hydrobromide (5.8g) in methylene chloride (100 mL) at 0° C. was treated with chlorotrimethylsilane (7.4 mL). After 4 hours, the reaction was filtered, washed with cold NaHCO₃, brine, dried (MgSO₄), filtered and evaporated to provide an oil. To a solution of the above oil in THF (100 mL), was added 3-(2-thienyl)propanoic acid (4.33 g) and 1-hydroxybenzotriazole (6.8 g) followed by the addition of dicyclohexylcarbodiimide (5.2 g). After 12 hours, the reaction was filtered and concentrated. The residue was taken up into EtOAc and refiltered. The organic solution was washed with 10% aq. NaHCO₃, 1 N HCl, brine, dried (MgSO₄), filtered and concentrated. Chromatography on silica gel (elution with 50% ethyl acetate/hexanes) provided 4.61 g of the desired product as a white solid.

EXAMPLE 15

1,2,3,4,-Tetrahydro-6-trimethylacetoxy-N-3-(2-thienyl)propionylisoquinoline

To a solution of the product of Example 14 (2.83 g) in trifluoroacetic acid (30 mL) at 0° C. was added dropwise trimethylacetyl chloride (1.4 mL) and the reaction allowed to warm to room temperature. After 4 hours, the reaction was quenched with water and concentrated, the residue was dissolved in $CH_2Cl_2$, washed with brine, dried (MgSO₄), filtered and concentrated. Chromatography of the residue on silica gel (elution with 50% ethyl acetate/hexanes) provided 3.8 g of desired product.

EXAMPLE 16

1,2,3,4-Tetrahydro-6-trimethylacetoxy-N-3-(2-thienyl)-propylisoquinoline methane sulfonate To a solution of the product of Example 15 (3.7 g) in THF (50 mL) at 0.C was added 20 mL of a 1 M borane•THF solution. After 2 hours at 0° C., the reaction was warmed to room temperature and allowed to stir an additional 4 hours. After removal of the solvent, the residue was taken up into Et₂O and treated with N-N-N'-N'-tetramethylethylenediamine (7.5 mL). After 3 hours, the reaction was filtered, washed with brine, dried (MgSO₄), filtered and concentrated. Chromatography of the resulting oil on silica gel (elution with 20% ethyl acetate/hexanes) provided 2.26 g of free base which was taken up into EtOAc and treated with a solution of methanesulfonic acid (0.42 mL) in i-PrOH (0.20 mL). Dilution of the resulting solution with Et₂O provided 2.1 g of the desired material, m.p. 155°–157° C. Anal. calcd. for $C_{21}H_{27}NO_2S \cdot \frac{1}{2}H_2O \cdot CH_3SO_3H$: C, 57.68; H, 6.93; N, 3.06. Found: C, 57.66; H, 6.81; N, 3.04.

EXAMPLE 17

1,2,3,4-Tetrahydro-6-((dimethylamino)carbonyl)oxy-2-N-(3-(2-thienyl)propionyl)isoquinoline To a solution of the product of Example 14 (1.5 g) in pyridine (10 mL) at 0° C. was added dropwise dimethyl carbamyl chloride (0.52 mL) and the resulting solution was heated at 70°–80° C. for 24 hours. The pyridine was removed and the reaction diluted with $CH_2Cl_2$, washed with water (3x), brine, dried (MgSO₄), filtered and concentrated. Chromatography of the residue on silica gel (elution with 1% $CH_2OH/CH_2Cl_2$) provided 1.29 g of the desired product.

EXAMPLE 18

1,2,3,4-Tetrahydro-6-((dimethylamino)carbonyl)oxy-2-N-(3-(2-thienyl)propyl)isoquinoline methane sulfonate Using the procedure outlined in Example 16, the product of Example 17 (1.29 g) was reduced to afford after chromatography on silica gel (elution with 30% ethyl acetate/hexanes) and salt formation 0.51 g of desired product, m.p. 160°–161° C. Anal. calcd. for C₁₉H₂₄N₂O₂S•CH₃SO₃H: C, 54.52; H, 6.41; N, 6.36. Found: C, 54.51; H, 6.36; N, 6.33.

EXAMPLE 19

6-Amino-1,2,3,4-terahydro-2-N-(3-phenylpropionyl) isoquinoline

To a solution of 6-amino-1,2,3,4-tetrahydroisoquinoline (2.5 g) and triethyl amine (2.8 mL) in CH₂Cl₂ (40 mL) at 0° C., is added dropwise hydrocinnamyl chloride (2.75 mL). After 8 hours the reaction is concentrated. The residue is taken up into a mixture of water and ethyl acetate. The layers are separated and the organic phase washed with 10% NaOH, brine, dried over MgSO₄, filtered and concentrated. Chromatography on silica gel will provide the desired product.

EXAMPLE 20

6-N-Methylamino-1,2,3,4-tetrahydro-2-N-(3-phenylpropyl) isoquinoline dihydrochloride A solution of Example 19 (1.5 g) and ethyl formate (12 mL) in toluene (20 mL) is heated at reflux for 2 hours. The reaction is cooled and concentrated. The residue is taken up into THF (20 mL), treated with 1.0 M solution of borane in THF (40 mL) and heated to reflux. After 12 hours, the reaction is cooled, treated with a saturated methanolic HCl solution and reheated to reflux. After 2 hours the reaction is cooled and concentrated. The residue can be crystallized from methanol/ethyl acetate to provide the desired material.

EXAMPLE 21

1,2,3,4-Tetrahydro-6-N,N'-dimethylamino-2-N-(3-phenylpropionyl)isoquinoline dihydrochloride A mixture of Example 19 (1.0 g) and 10% Pd/C (0.75g) in methanol (200 mL) containing formalin (5 mL) is hydrogenated at room temperature under 4 atm. of hydrogen. After the reaction is complete, the mixture is filtered and concentrated. The residue is taken up into ethyl acetate, washed with brine, dried over MgSO₄, filtered and concentrated. Chromatography on silica gel will provide the desired product as its free base. This material can be converted to its hydrochloride salt as described in Example 4.

EXAMPLE 22

1,2,3,4-Tetrahydro-6-methylsulfonamido-2-N-(3-phenylpropionyl)isoquinoline

To a solution of Example 19 in pyridine (10 mL) at 0° C. is added dropwise methanesulfonyl chloride (0.86 mL). After 45 minutes at 0° C., the reaction is allowed to warm to room temperature and stirred an additional 30 minutes. The pyridine is removed and the residue taken up into CH₂Cl₂ and washed with 10% HCl. The organic phase is washed with brine, dried over MgSO₄, filtered and concentrated. Chromatography on silica gel will provide the desired material.

EXAMPLE 23

1,2,3,4-Tetrahydro-6-methylsulfonamido-2-N-(3-phenylpropyl)isoquinoline hydrochloride Using the procedure outlined in Example 2, the product of Example 22 can be reduced to afford after chromatography and salt formation the desired product.

EXAMPLE 24

1,2,3,4-Tetrahydro-6-(N-methyl-(methylsulfonamido))-2-N-(3-phenylpropyl)isoquinoline hydrochloride To a suspension of sodium hydride (0.17 g) in dimethylformamide (10 mL) at 0 C is added a solution of Example 22 (1.0 g) in dry dimethylformamide (10 mL). After stirring for 30 minutes, the reaction is treated with methyl iodide (0.5 mL), warmed to room temperature and allowed to stir for 12 hours. The reaction mixture is poured into cold 10% HCl and the product extracted out with CH₂Cl₂. The organic phases are combined, washed with brine, dried over MgSO₄, filtered and concentrated. Using the procedure outlined in Example 2, the resulting residue can be reduced to provide after chromatography on silica gel and salt formation the desired product.

EXAMPLE 25

6-Fluoro-1,2,3,4-tetrahydro-N-(3-phenylpropyl) isoquinoline hydrochloride

Using the procedures in Examples 1 and 2, but replacing 3-(2-thienyl)propanoic acid with 3-phenylpropanoic acid and 1,2,3,4-tetrahydro-6-methoxyisoquinoline with 6-fluoro-1,2,3,4-tetrhydroisoquinoline affords the desired product.

The compounds were assessed for alphaadrenergic receptor subtype selectivity by use of radioligand binding techniques as described previously (DeBernardis et al., J. Med. Chem. 28, 1398 (1985)). Affinity for the alpha-1-receptor was assessed using rat liver homogenates and the radioligand [³H]-pyrazosin; whereas for the alpha-2-receptor, rat cerebral cortices and the radioligand [³H]-rauwolscine were utilized. Results obtained from the binding studies are shown in Table 1 for a representative sample of compounds disclosed herein, showing clearly the excellent affinity for the alpha-2-receptor, as well as the high degree of selectivity relative to the alpha-1-receptor.

TABLE 1

| Radioligand Binding Data at Alpha-1 and Alpha-2 Adrenoceptors for Representative Compounds | | | |
|---|---|---|---|
| | $K_i$(nM) | | Alpha-2 Selectivity |
| Example # | alpha-1 | alpha-2 | $K_i\alpha_1/K_i\alpha_2$ |
| 2 | 150 | 4.3 | 35 |
| 5 | 206 | 4.6 | 45 |
| 6 | 154 | 2.2 | 69 |
| 7 | 217 | 5.9 | 37 |
| 8 | 174 | 10.7 | 16 |
| 13 | 114 | 5.6 | 20 |

In order to evaluate antiglaucoma activity, the test compounds were dissolved in the vehicle, a 0.2% aqueous solution of hydroxymethylcellulose at various concentrations such as 0.03%, 0.1%, or 0.3%. Comparisons were made to the reference standard, pilocarpine hydrochloride which was dissolved in the vehicle at a concentration of 0.5%. Control treatment was a volume dose of vehicle.

Male, albino New Zealand rabbits (Scientific Animal Farms and/or Kuiper's Rabbit Ranch) weighing 2.06–2.5 kg were used in the study. Intraocular pressures were obtained in the normal eyes of the animals using a Bausch and Lomb Applamatic Tonometer. Three separate sessions provided the baseline pressures for each eye. The test compound or vehicle (0.1 mL) was instilled into the eyes of 6 different rabbits according to a randomized dosing schedule. Intraocular pressures were taken at 5, 15, 30, 45, 60, 90 and 120 minutes after instillation of the test compounds.

Statistical treatment was by one-way analysis of variance. Results are shown (Table 1) for a representative sample of the compounds claimed.

TABLE 2

| | Percent Change in IOP vs Baseline - Minutes after Administration | | | |
|---|---|---|---|---|
| | Time After Administration (Minutes) | | | |
| Compound | 5 | 15 | 90 | 120 |
| Example 2[a] | −50 | −41 | −13 | +8 |
| Example 16[a] | −11 | −12 | −36 | −4 |
| Example 18[a] | −38 | −26 | −48 | −12 |
| Pilocarpine[b] | — | −22 | −20 | −33 |

[a]0.3% solution
[b]0.5% solution

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

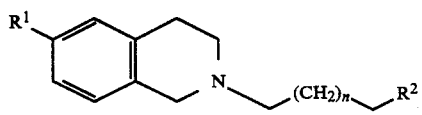

wherein n=1 or 2; $R_1$ is lower alkoxy, lower alkyl, halo, ester, carbamate, or substituted amino; and $R_2$ is thienyl or furyl; or $R_2$ is

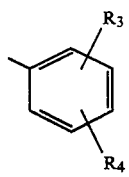

wherein $R_3$ and $R_4$ are independently selected from hydrogen, halo, and methoxy; and pharmaceutically acceptable salts thereof.

2. A compound as in claim 1 that is selected from the group consisting of:
1,2,3,4-tetrahydro-6-methoxy-N-3-(2-thienyl) propylisoquinoline hydrochloride;
1,2,3,4-tetrahydro-6-methoxy-N-4-(2-thienyl) butylisoquinoline hydrochloride; and
1,2,3,4-tetrahydro-6-methyl-N-3-(2-thienyl) propylisoquinoline hydrochloride.

3. A pharmaceutical composition for selectively inhibiting alpha-2-adrenergic receptors comprising a pharmaceutically acceptable carrier and a therapeutically effective amount of a compound of the formula:

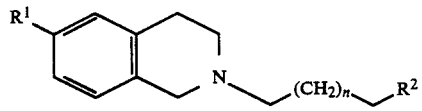

wherein n=1 or 2; $R_1$ is lower alkoxy, lower alkyl, halo, ester, carbamate, or substituted amino; and $R_2$ is thienyl or furyl; or $R_2$ is

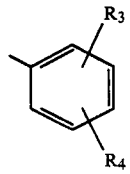

wherein $R_3$ and $R_4$ are independently selected from hydrogen, halo, and methoxy; and pharmaceutically acceptable salts thereof.

4. A composition as in claim 3 wherein the compound is selected from the group consisting of:
1,2,3,4-tetrahydro-6-methoxy-N-3-(2-thienyl) propylisoquinoline hydrochloride;
1,2,3,4-tetrahydro-6-methoxy-N-4-(2-thienyl) butylisoquinoline hydrochloride: and
1,2,3,4-tetrahydro-6-methyl-N-3-(2-thienyl) propylisoquinoline hydrochloride.

5. A method for selectively inhibiting alpha-2-adrenergic receptors comprising administering to a patient in need of such treatment, a therapeutically effective amount of a compound of the formula:

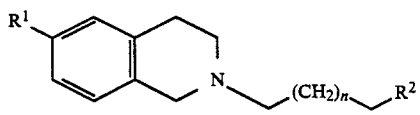

wherein n=1 or 2; $R_1$ is lower alkoxy, lower alkyl, halo, ester, carbamate, or substituted amino; and $R_2$ is thienyl or furyl; or $R_2$ is

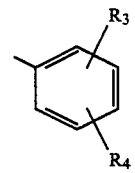

wherein $R_3$ and $R_4$ are independently selected from hydrogen, halo, and methoxy; and pharmaceutically acceptable salts thereof.

6. A method for treating glaucoma comprising administering to a patient in need of such treatment, a therapeutically effective amount of a compound of the formula:

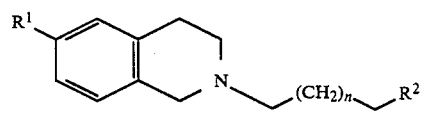

wherein n=1 or 2; $R_1$ is lower alkoxy, lower alkyl, ester, carbamate, or substituted amino; and $R_2$ is thienyl or furyl; or $R_2$ is

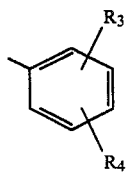

wherein R3 and R4 are independently selected from hydrogen, halo, and methoxy; and pharmaceutically acceptable salts thereof.

7. A method as in claim 6 wherein the compound is selected from the group consisting of:
1,2,3,4-tetrahydro-6-methoxy-N-3-(2-thienyl) propylisoquinoline hydrochloride;
1,2,3,4-tetrahydro-6-methoxy-N-4-(2-thienyl) butylisoquinoline hydrochloride; and
1,2,3,4-tetrahydro-6-methyl-N-3-(2-thienyl) propylisoquinoline hydrochloride.

* * * * *